United States Patent [19]

Broder et al.

[11] Patent Number: 4,722,888

[45] Date of Patent: Feb. 2, 1988

[54] CELL LINE PRODUCING HUMAN MONOCLONAL ANTIBODY WHICH BINDS TO HTLV-I PRODUCING CELLS

[75] Inventors: Samuel Broder, Bethesda; Shuzo Matsushita; Marjorie Robert-Guroff, both of Rockville, all of Md.

[73] Assignee: United States of America as represented by the Department of Health and Human Services, Washington, D.C.

[21] Appl. No.: 717,613

[22] Filed: Mar. 29, 1985

[51] Int. Cl.[4] .................. C12Q 1/70; G01N 33/53; G01N 33/577; A61K 39/42
[52] U.S. Cl. .............................. 435/5; 435/7; 435/68; 435/240.27; 435/172.2; 436/518; 436/536; 436/548; 436/811; 436/813; 935/100; 935/104; 935/108; 935/110; 424/86; 530/387; 530/389; 530/826; 422/61
[58] Field of Search .............. 435/5, 7, 68, 240, 172.2; 436/518, 536, 548, 811, 813; 935/100, 104, 108, 110; 422/61; 530/387, 389, 826

[56] References Cited

U.S. PATENT DOCUMENTS 4,588,681  5/1986  Sawada .................................. 435/5

OTHER PUBLICATIONS

Papas et al., Chemical Abstracts, 102 (1985) #198975.
Koyanagi et al., Med. Microbiol. Immunol., 173 (1984), 127-140.
Lee et al., Proc. Natl. Acad. Sci. U.S.A., 81 (1984), 3856-3860.

*Primary Examiner*—Christine M. Nucker
*Attorney, Agent, or Firm*—John S. Roberts, Jr.

[57] ABSTRACT

The present invention is an immortalized B-cell line which produces a human monoclonal antibody IgG-Kk which specifically binds to the envelope antigen of human T-cell leukemia virus Type 1 (HTLV-I). This monoclonal antibody is useful as a diagnostic reagent by binding to the antigen specifically expressed on the surface of HTLV producing cells. Furthermore, this monoclonal antibody is useful as a therapeutic reagent, in combination with complement, for the lysis of HTLV-1 producing cells.

9 Claims, 4 Drawing Figures

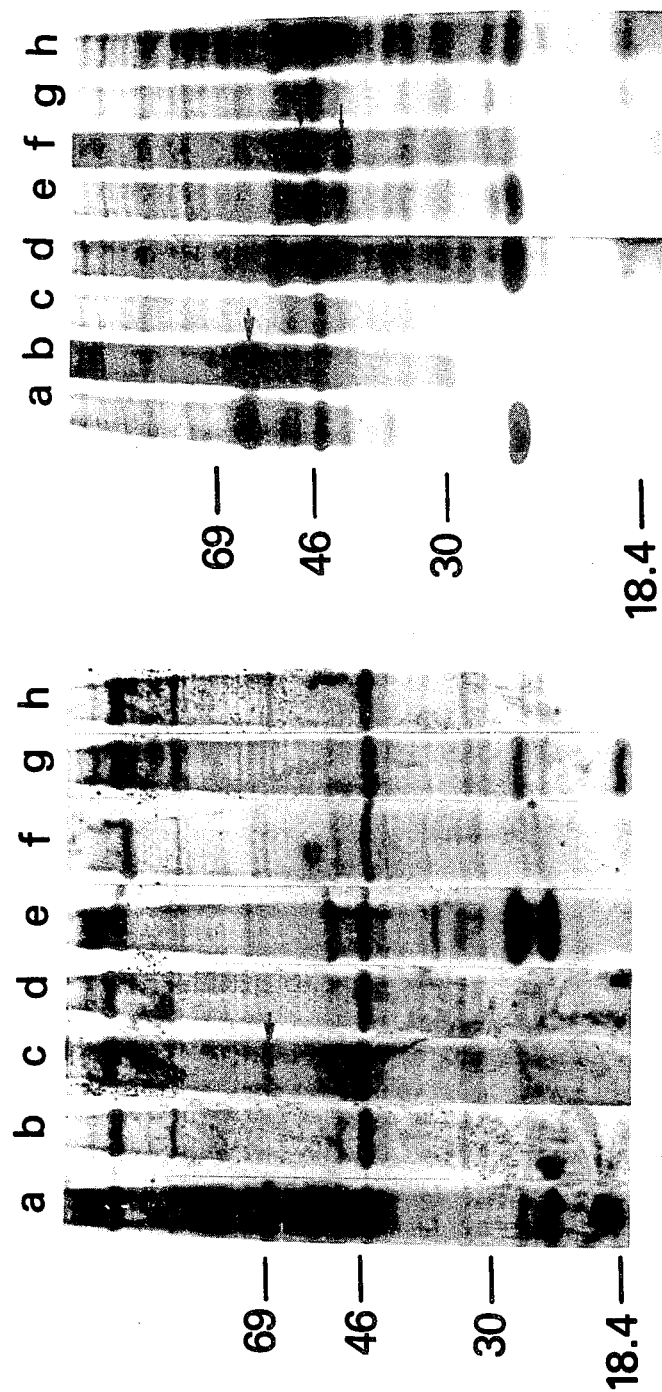

CELL LINE PRODUCING HUMAN MONOCLONAL ANTIBODY WHICH BINDS TO HTLV-I PRODUCING CELLS

BACKGROUND

The human T-cell leukemia viruses (HTLV) are family of exogenous human retroviruses with three known types. HTLV type-I (HTLV-I) is etiologically associated with adult T-cell leukemia-lymphoma (ATL), first described clinically in Japan, and found endemic to southern Japan, the Caribbean Basin, and certain parts of Africa. HTLV type-II (HTLV-II) was isolated from a patient with a T-cell variant of hairy cell leukemia. Although serological cross-reactivity between HTLV-I and II has been reported, these two viruses differ significantly in antigen assays and in their genomes. A third subgroup of HTLV (HTLV-III) refers to a prototype virus isolated from patients with acquired immune deficiency syndrome (AIDS).

Specific antibodies to HTLV-I have been detected in ATL patients and in asymptomatic carriers. These antibodies are known to recognize both gag and env protein of the virus. Viral gag proteins have been purified, sequenced, and murine monoclonal antibodies against these core proteins (p19, P24) have been produced and extensively used for detecting core antigens. However, viral envelope proteins, important for viral infection, have not been well characterized. Murine monoclonal antibody to a minor component of envelope protein (gp21 or p20E) has been reported, but a monoclonal antibody to the major component of envelope protein (gp46) has not yet been produced. The present invention discloses the production of a monoclonal antibody which specifically binds to the major HTLV-I envelope protein (gp46). Furthermore, the present invention discloses an immortalized cell line, designated 0.5 alpha, which secretes this monoclonal antibody.

STATEMENT OF DEPOSIT

Cell line 0.5 alpha, the B-cell line which produces the anti-HTLV-I monoclonal antibody of this invention, was deposited in the American Type Culture Collection on Mar. 19, 1985 under accession number HC8755. The cell line will be maintained for a period of thirty years from the deposit date, or until at least five years after the most recent request for a sample, whichever is longer. Furthermore, the cell line will be available to the public once a patent on said cell line issues.

DESCRIPTION OF THE FIGURES

FIG. 4. is the electrophoresis illustration of Example 9.

SPECIFIC DESCRIPTION

Figure 1:
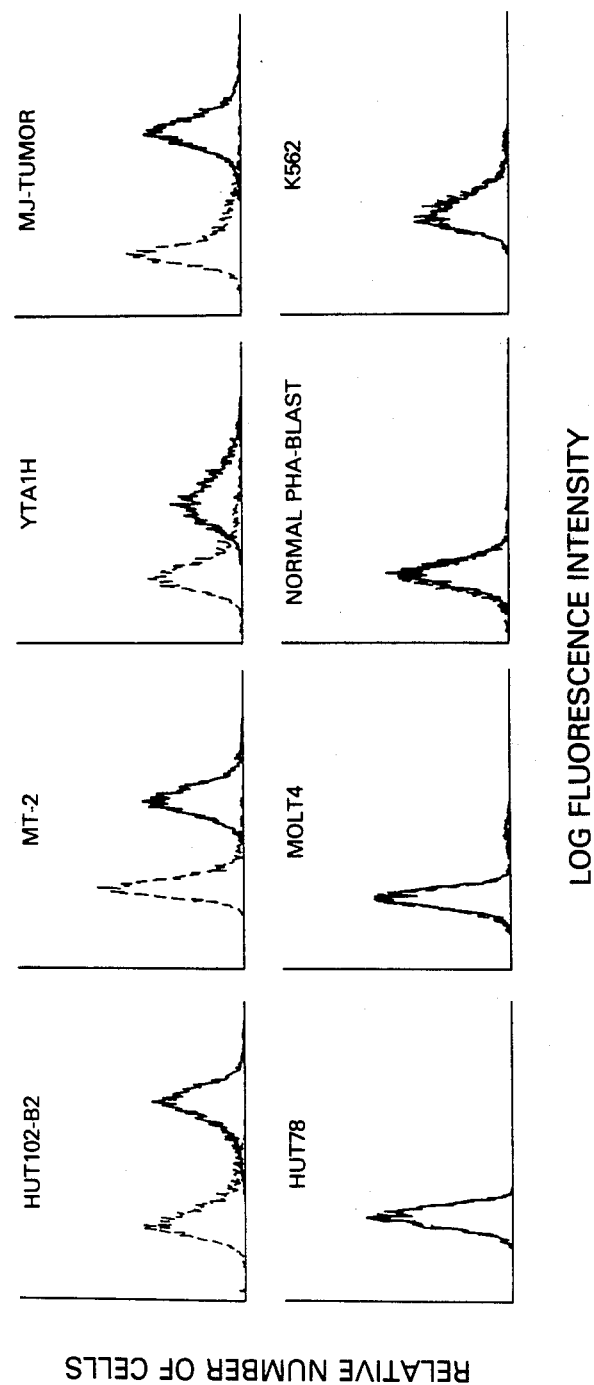
FIG. 1. Compares FACS profiles of four HTLV-I producing cell lines with four HTLV-I negative cell lines. See Example 7 for additional description.

The human B-cell clone of this invention secretes an IgG (k) monoclonal antibody which specifically binds to the envelope protein (gp46) found on the cell membrane of HTLV-I-producing cells. This cell line, designated 0.5α, was derived from a patient with HTLV-I infection, and immortalized using the Epstein-Barr virus technique. As noted in the examples, the cell line was cloned in vitro by the limiting dilution technique.

Most importantly, cell line 0.5α produces an IgG-K antibody which specifically binds to the major envelope protein of HTLV-I, but does not bind to HTLV-I-negative T-cells. The monoclonal antibody detects a 46kd glycoprotein (gp46) found in disrupted HTLV-I virions. As shown in Example 4, 0.5α also detects a 34kd protein produced after endoglycosidase-F treatment of HTLV-I. In short, 0.5α binds to a viral glycoprotein of 46kd (gp46) and also binds to a gp46 protein moiety of 34kd. These proteins are the major envelope glycoprotein of HTLV-I.

While the above-noted characteristics of 0.5α monoclonal antibody are of diagnostic value, this monoclonal antibody, combined with complement, is also of therapeutic value. In combination with complement, monoclonal antibody 0.5α lyses HTLV-I producing cells but does not lyse HTLB-I negative cells. Table 1 summarizes the complement dependent cytotoxic ability of 0.5α monoclonal antibody. Note that only HTLV-I producing cell lines were lysed by complement-aided 0.5α.

The method of diagnosing and treating HTLV-I may be incorporated into a test kit comprising:

1. monoclonal antibody 0.5α or a cell line (e.g. ATCC# HC8755) secreting a monoclonal antibody specific for HTLV-I envelope protein.
2. complement; and
3. enzyme-linked-immunosorbent assay (ELISA) means or trypan blue dye exclusion test means including an insoluble immunosorbent in bead, strip, plate, or test cavity form, enzyme or dye for labeling.

EXAMPLES

Example 1

Non T-cells were separated from lymph node cells obtained from a seropositive patient with ATL by rosetting with sheep erythrocytes and exposing them to Epstein Barr virus (EBV). After 11 days in culture these cells were cloned by the limiting dilution technique. Several B-cell clones were obtained after about one month in culture. The supernatants of these clones were screened by enzyme-linked-immunosorbent assay (ELISA), detecting HTLV-I specific antibody by comparing the binding activity of antibody to HTLV-I-producing cells and HTLV-I-negative cells. Among them, the supernatant from a clone derived from a well which was plated with 0.5α cells was reacted specifically to HTLV-I-producing cells. This human B-cell clone, designated 0.5α duplicated slowly after cloning (approximately 6 days for doubling) and secreted about 5 ug/ml of monoclonal IgG (k) antibody in 6 days in culture at the initial cell concentration of $3 \times 10^5$/ml.

0.5α was continuously cultured in RPMI 1640 supplemented with 10% heat-inactivated fetal calf serum, 4 mM l-glutamine, 50 ul/ml penicillin and 50 ul/ml streptomycin, and maintaining production of specific antibody for over 7 months. All of the 8 subclones cloned from 0.5α secreted monoclonal antibody that exhibit the same specificity.

Example 2

The reactivity of this human monoclonal antibody 0.5α was tested with various cell lines and disrupted viral preparation of HTLV-I, II, and III by using ELISA. 0.5α reacted only with HTLV-I producing cell lines and disrupted HTLV-I virus, but not HTLV-I negative cells and disrupted HTLV-II and III viruses. The binding activity of this antibody to the surfaces of living cells was tested by fluorescence activated cell sorter (FACS). FACS quantifies antibody binding to particular cell populations by immunofluorescence, displaying more brightly stained populations (those which bind more antibodies) to the right of less brightly stained populations. FIG. 1 shows representative FACS profiles with four HTLV-I producing cell lines in contrast to four HTLV-I-negative cell lines. The monoclonal antibody 0.5α bound to the surface membrane of HTLV-I producing cells, but not to HTLV-I negative cells. This binding was detected in 100% of the HTLV-I producing cell population. As summarized in the table, 0.5α bound neither to HTLV-I negative cell lines, nor to HTLV-II producing C3-44 or HTLV-III producing H9/IIIb cells or to mitogen (phytohemagglutinin, PHA) stimulated normal peripheral blood mononuclear cells (PHA-blast) and normal peripheral T-cell separated by sheep erythrocytes rosetting. Moreover, the T-cell lines derived from a single seronegative donor HTLV-I infected (YTA1H and STH4) were positive for expression of the antigen while uninfected mature T-cell clone (YTA1 and PHA) stimulated T-cells were negative. Also tested was the binding activity of 0.5α to cryopreserved fresh peripheral leukemic T-cells from four ATL patients. However, no specific binding of 0.5α to these fresh leukemic cells was detected.

Example 3

Figure 2:
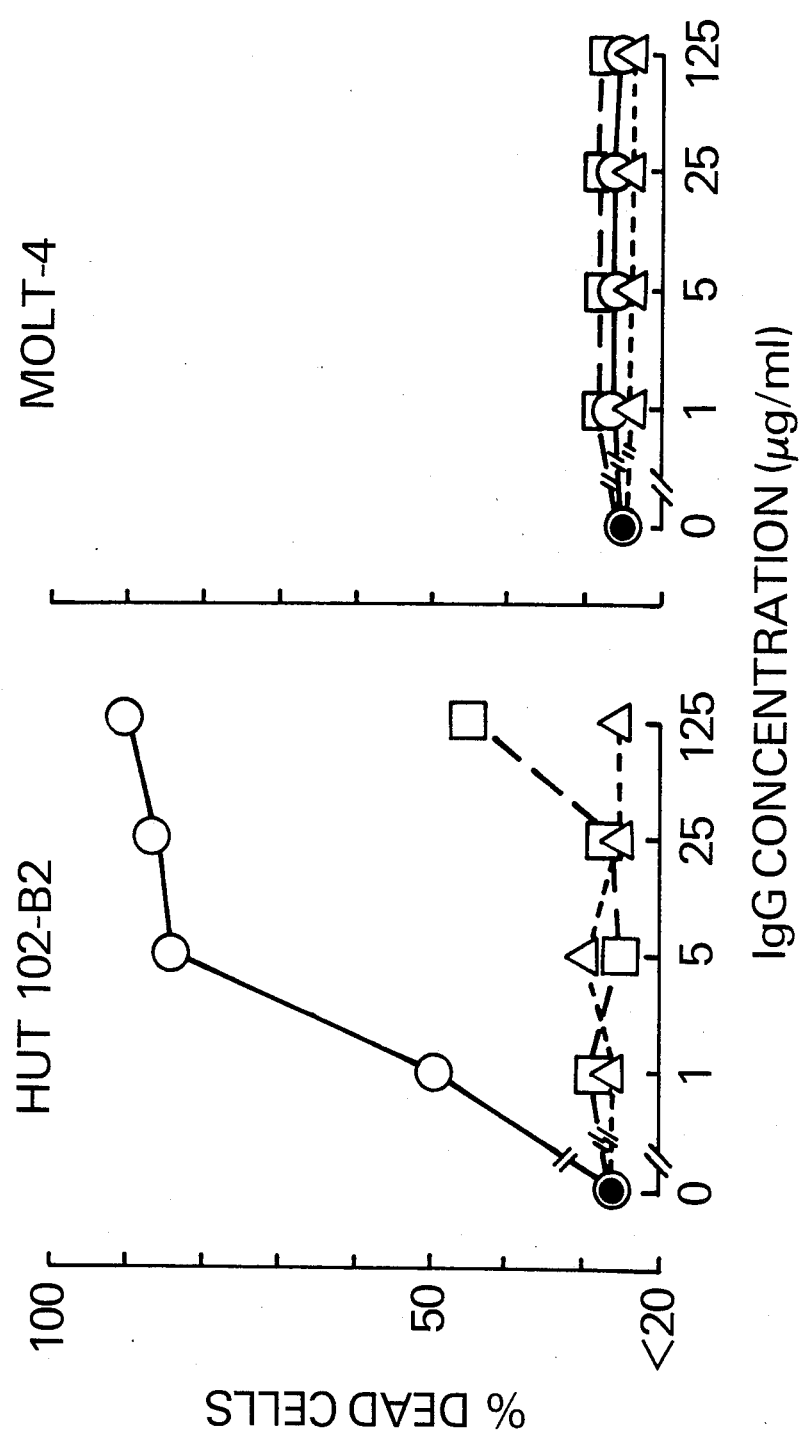
FIG. 2. Complement dependent cytotoxicities of monoclonal antibody 0.5α. $2.5 \times 10^5$ of target cells (HUT 102-B2, MOLT-4) were incubated for 30 minutes at room temperature with various concentration of protein-A purified IgG fraction of 0.5a (O—O), IgG fraction of serum from ATL patient (□—□) and IgG from normal donor (Δ—Δ) in 50 ul of RPMI 1640 containing 5% heat inactivated fetal calf serum. Then 30 ul of rabbit complement were added to each cultures and incubated for 1 hour at 37° C. The percentages of dead cells were determined by the trypan blue dye-exclusion test. Control cytotoxicity with complement alone is indicated ( ⊙ ).

The complement dependent cytotoxic activity of 0.5α was tested using trypan blue dye exclusion test. As shown in FIG. 2, 0.5α killed HTLV-I producing HUT-102 cells in the presence of complement, but did not kill HTLV-I-negative Molt-4 cells even in high concentration of antibodies. Protein-A purified polyclonal IgG from a patient with ATL who had high titer of anti-HTLV antibody could also lyse HUT 102 cells specifically. These antibodies were not cytotoxic without complement. As summarized in the table, this complement dependent killing activity of 0.5α was tested for various cell lines. Only HTLV-I producing cell lines were lysed by 0.5α in the presence of rabbit complement. These data show that human monoclonal antibody 0.5α binds to the antigen specifically expressed on the surface of HTLV-I producing cells and can lyse such cells in the presence of complement.

Example 4

Figure 3B:
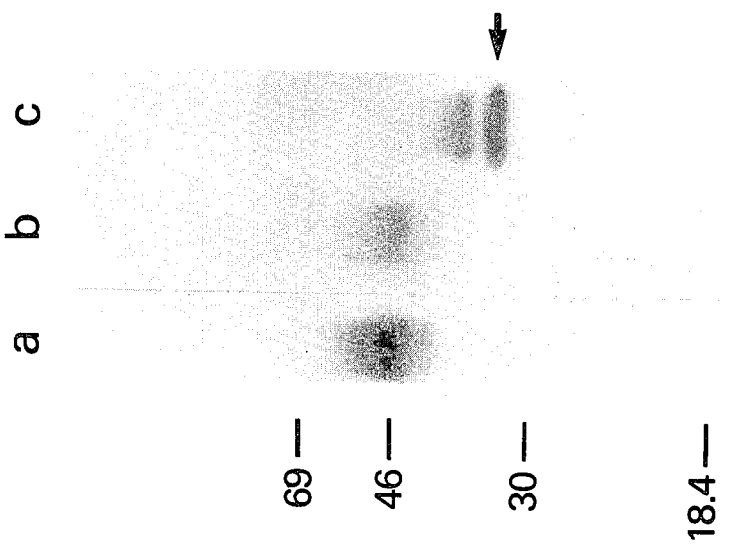
FIG. 3. Illustrates the experiment of Example 8 with regard to specificity of monoclonal antibody 0.5α to the gp46 envelope protein and its precursor glycoprotein gp61.
Figure 3A:
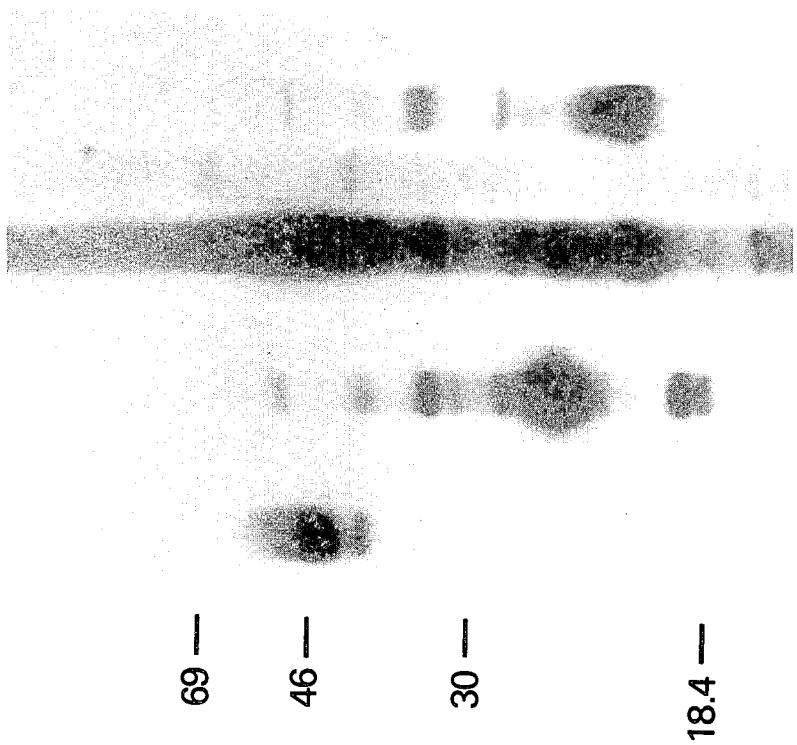

Tests were conducted to determine the antigen molecule detected by 0.5α analyzing disrupted virus by Western blot technique. As shown FIG. 3-A lane a, 0.5α detected viral protein of approximate molecular weight 46,000 daltons as a distinct band. While antibodies to viral core proteins (p24; lane c, p19, lane g) did not detect the same molecule, a serum from ATL patient detected the same antigen as a broader band. Disrupted HTLV-II and III viruses was also analyzed with 0.5α in the same electroblot assay but nothing was detected by 0.5α. HTLV-I virus was treated with endoglycosidase-F (FIG. 3-B) and analyzed with 0.5α by Western blot. The monoclonal antibody detected protein with approximate molecular size of 34,000 daltons after endoglycosidase-F treatment (FIG. 3-B, lane c, indicated by arrow), while the same buffer treatment alone did not change the molecular weight of the antigen (FIG. 3-B, lane b). This shows that 0.5α binds to a viral glycoprotein of molecular size 46,000 daltons (gp46), and also binds to the protein moiety of gp46 of molecular size 34,000 daltons. This viral antigen gp46 is the major component of viral envelope protein.

Example 5

The antigen detected by 0.5α was further examined by immunoprecipitation of metabolically labeled cell lysates. FIG. 4 demonstrates that monoclonal antibody 0.5α immunoprecipitated the antigens of 68,000 daltons (gp68) from MT-2 cells (FIG. 4-A, lane c) and 61,000 daltons (gp61) from HUT102 cells (FIG. 4-B, lane b). Radiolabelled cell lysates from MT-2 cells were also precipitated by antibody to core protein (p24; FIG. 4A, lane e, p19; FIG. 4A, lane g). These antibody to gag protein precipitated both mature protein p24 and p19 and their precursor polyprotein p28 and p54, but did not precipitate gp68; 0.5α precipitated only gp68. As a positive control, ATL patient's serum precipitated both gp68 and gag related proteins (FIG. 4-A, lane a). HUT102 cells were also metabolically labelled in the presence of tunicamycin and immunoprecipitated with 0.5α (FIG. 4-B, lane f). Gp61 disappeared and two major bands of molecular size 46,000 and 41,000 daltons were precipitated by 0.5. The precipitation of gag related protein by patient's serum (FIG. 4-B, lane a,e) and goat anti-serum to p24 (FIG. 4-B, lane d,h) was not affected by tunicamycin treatment. Similar results were obtained by immunoprecipitating tunicamycine treated MT-2 cell lysate. These results show that the antigen 0.5α precipitates is a glycoprotein of gp61 from HUT102 cells and gp68 from MT-2 cells. Similar glycoproteins have been reported as precursor proteins of HTLV-I envelope. After tunicamycin treatment, these glycoproteins were no longer synthesized and two proteins of p46 and p41 were precipitated by 0.5α.

Example 6

Human monoclonal antibody 0.5α specifically binds to surface membrane of HTLV-I producing cells and kills such cells in the presence of complement. In animal retroviruses, envelope proteins are expressed on the surface of infected cells and specific antibody to envelope protein can lyse the virus producing cells. Moreover, the antigen(s) specifically expressed on the membrane of HTLV-I infected cells are related to envelope glycoprotein(s). These observations suggest that the monoclonal antibody is specific for the envelope protein of HTLV-I but, does not completely exclude the possibility the antigen recognized by 0.5α is cellular antigen specifically induced by HTLV. However, further analysis of the antigen(s) detected by 0.5α revealed that the antigen was a glycoprotein which has the same mobility and deglycoslation pattern of HTLV-I envelope protein that described. Moreover, the particular patient that 0.5α was derived from had antibody to gp61 (HUT102). Some patients with ATL have antibodies that compete the binding of 0.5α to HTLV-I. These results suggest this human monoclonal antibody 0.5α binds to the antigen that has been reported as major envelope protein of HTLV-I.

Example 7

Representative FACS profiles of cells stained with human monoclonal antibody 0.5α. Profiles representing cells populations stained with 0.5α and FITC-conjugated goat anti-human IgG are represented by solid lines (—) while control population stained with the equal amount of normal human IgG and FITC-conjugated anti-human IgG are represented by broken lines (- - - - - -). HUT102, MT-2 and MJ-Tumor cells are long term cultured human T-cell lines known to produce HTLV-I. YTA1H is HTLV-I infected clonal T-cell from tetanus toxoid specific uninfected normal clone YTA1 as described. PHA-blast cells were prepared from 14 days cultivation of PHA stimulated periperal blood mononuclear cells obtained from the same seronegative donar that YTA1H was derived from. MOLT-4 and HUT 78 are human T-cells lines known to be negative for HTLV-I. K562 is human erythroid leukemic cell line negative HTLV-I. Cells were grown in RPMI 1640 supplemented with 10% heat-inactivated fetal calf serum, 4 nM 1-glutamine, 50 u/ml penicillin and 50 ug/ml streptomycin (complete media) except YTA1 and PHA-blast cells were grown in the presence of 10% TCGF (vol/vol). $5 \times 10^5$ of each cells were incubated with 100 ul of 0.5α culture supernatant (approximately 5 ug/ml) or the same amounts of normal human IgG for 30 minutes at room temperature. Cells were washed twice with phosphate buffered saline (PBS) supplemented with 2% bovine serum alubumin (BSA) and 0.2% sodium azide (BSA-PBS). Subsequently, cells were incubated with FITC-conjugated anti-human IgG diluted 1:20 in BSA-PBS for 30 minutes at 4° C. Cells were then washed twice in BSA-PBS and resuspended in the same buffer. These statined cells were analyzed on fluorescence activated cell sorter.

Example 8

(A) Recognition of envelope protein (gp46) of HTLV-I by human monoclonal antibody 0.5α. Culture supernatant of 0.5α diluted approximately 100 ng/ml (FIG. 3, lane a), equal amount of normal human IgG (lane b), amniospecific goat antiserum to p24 diluted 1:250 (lane c), equal dilution of normal goat serum (lane d), serum from a patient with ATL diluted 1:100 (lane e), normal serum with the same dilution (lane f), murine monoclonal antibody to p19 diluted 1:1000 (lane g), and the same dilution of control mouse ascites P3 (lane h) were analyzed in a strip RIA based on the Western blot technique. Briefly, 200 ug of double banded HTLV was electrophoresed under reducing conditions on a preparative sodium dodecyl sulfate (SDS) polyacrylamide slab gel and transferred electrophoretically to a nitrocellulose sheet. Strips cut from the sheet were reacted with antibodies listed above. Bound antibodies were made visible with radiolabelled protein-A. 0.5α detected a molecule of approximate molecular weight 46,000 daltons which is clearly distinguishable with those of gag proteins. (B) Detection of protein moiety of gp46 by 0.5α after endoglycosidase F treatment of the virus. Double banded disrupted HTLV-I (100 ug) was treated with 10 u of endoglycosidase F in 0.1M sodium phosphate buffer (ph 6.7), 1% Nonidet P-40, 0.1% SDS, 1%-mercaptoethanol, and 25 mM EDTA for 6 hours at 37° C. Disrupted virus was also treated with the same buffer without endoglycosidases F as a control. The mixtures were dialyzed extensively against 10 mM ammonium bicarbonate and lyophilized. These samples and nontreated virus were dissolved in Laemmli's sample buffer, electrophoresed and blotted in the same way described above. Then the blotted nitrocellulose sheet was reacted with diluted supernatant of 0.5α at a concentration of 100 ng/ml IgG. Bound antibodies were detected by radiolabelled protein-A. The smaller molecule of 34,000 daltons (indicated by arrow) was detected after endoglycosidase F treatment (lane c), while the same buffer treatment without enzyme (lane b) did not change the molecular size from the virus preparation with no treatment (lane a).

Example 9

(A) Immunoprecipitation of gp68 from metabolically labelled MT-2 cell lysate by human monoclonal antibody 0.5α. MT-2 cells were exposed to ($^{35}$S) cysteine (100 uci/ml) for 3 hours. A soluble cell lysate was obtained by disruption with RIPA buffer (0.15M NaCl, 0.05M tris HCl, PH 7.2, 1% Triton X-100, 1% sodium deoxycholate, 0.1% SDS) and centrifuged for 1 hour at 10,000 g. The lysate supernatant was cleared once with 10 ul of normal control serum that is negative for anti-HTLV antibody bound to protein A CL-4B (protein A beads) before portions were reacted with 101 of the following antibodies preabsorbed with protein-A beads: (a) 20 ul of serum from a patient with ATL, (b) 20 ul of serum from seronegative normal donor, (c) 20 ul of concentrated supernatant of 0.5α, (d) equivalent amount of normal human IgG, (e) 20 ul of goat antiserum to purified p24 of HTLV, (f) 20 ul of normal goat serum, (g) 20 ul of murine monoclonal antibody to p19 of HTLV, (h) equivalent amount of P3 ascites. Immunoprecipitates were deluted in Laemmli's sample buffer by boiling for 2 minutes. Samples were analyzed in a 12 percent SDS-polyacrylamide gel electrophoresis (SDS-PAGE). 0.5α precipitated a molecule of molecular size 68,000 daltons which is distinct from gag related proteins. (B) Immunoprecipitation of a glycoprotein (gp61) from radiolabelled HUT102 with or without tunicamycin. HUT102 cells grown in RPMI 1640 medium containing 10% fetal calf serum were pretreated for 2 hours with or without 10 ug/ml of tunicamycin, then exposed to 250 uci of ($^{35}$S) cystein in the presence or absence of 10 ug/ml of tunicamycin for 4 hours. Soluble lysates were obtained by disruption with RIPA buffer and centrifuged. The lysates were cleared once with 10 ul of normal reference serum bound to protein-A beads and the portions of extracts prepared from tunicamycin untreated cells (FIG. 4, a-d) and treated cells (FIG. 4, e-h) were reacted with 10 ul of the positive control serum from an ATL patient (a,e), protein-A column purified 0.5α containing 10 ug of IgG, 10 ul of normal negative control serum (c,g), and 10 ul of monospecific goat antiserum to p24 gag protein of HTLV (d,h) preabsorbed with protein-A beads. Immunoprecipitates were analyzed in a 12 percent SDS-PAGE as described in (A). 0.5α precipitated a molecule of 61,000 daltons (gp61) without tunicamycin treatment and also precipitated two molecules of 46,000 and 41,000 daltons with tunicamycin treatment (indicated by small arrow).

TABLE I

Summary of FACS analysis and complement dependent cytotoxicity of monoclonal antibody 0.5α. FACS analysis ws performed as described in FIG. 1. Cytotoxicity assay was performed as described in FIG. 2. HTLV producing YTA1H and STH4 were derived from the same seronegative healthy donor that YTA1 and one of PHA stimulated T-cells were derived from. Fresh peripheral T-cells were prepared by sheep erythrocytes rosetting. nd: not done.

| Cells | % Positive cells by FACS analysis | Complement mediated killing with 0.5 |
|---|---|---|
| HTLV-I positive cell lines | | |
| HUT 102-B2 | 96 | + |
| MT-2 | 97 | + |
| MJ-Tumor | 97 | + |
| YTA1H | 81 | nd |
| STH4 | 85 | + |
| HTLV-II positive cell line | | |
| C3-44 | 1 | — |
| HTLV-III positive cell line | | |
| H9/IIIb | 0 | — |
| HTLV negative cell lies | | |
| YTA1 | 0 | nd |
| H9 (uninfected) | 2 | — |
| HUT 78 | 0 | — |
| MOLT-4 | 0 | — |
| CCRF-CEM | 0 | — |
| K562 | 0 | nd |
| Daudi | nd | — |
| PHA-blast from two normal donors | 0 | — |
| T-cells from two normal donors | 0–4 | — |
| T-cells from cryopreserved peripheral blood mononuclearcells from four ATL patients | 0–6 | — |

We claim:

1. A cell line deposited with the American Type Culture Collection under accession number HC8755 which is capable of secreting an IgGk monoclonal antibody.

2. A reagent for the diagnosis of HTLV-I carriers comprising a 0.5 alpha human IgGk monoclonal antibody secreted by the cell line of claim 1 which specifically binds to the 46 kd envelope protein of human T-cell leukemia virus Type I combined with a pharmaceutically acceptable carrier.

3. A composition of matter comprising cells of the cell line of claim 1 in a culture media.

4. A composition of matter of claim 3 which further contains serum as part of the culture media.

5. A composition of matter containing IgGk monoclonal antibody produced by the cell line of claim 1.

6. A composition of matter of claim 5 further containing B-cells.

7. A method of detecting HTLV-I virus comprising the steps of:
   (1) Contacting cells susceptible to infection with HTLV-I with monoclonal antibodies of claim 2;
   (2) Adding patient serum or non-infected donor serum to paired samples of the cell/antibody mixture for comparison;
   (3) Adding complement to the mixture of (2); and
   (4) Inspecting the compositions of (3) after a suitable time to determine the extent of T-cell antibody reaction.

8. A kit for use in detecting HTLV-I infection consisting of:
   (1) A container having monoclonal antibodies of claim 5; and
   (2) A container having therein complement.

9. A kit of claim 8 further containing conjugated antihuman IgG in a container.

* * * * *

UNITED STATES PATENT AND TRADEMARK OFFICE
CERTIFICATE OF CORRECTION

PATENT NO. : 4,722,888

DATED : February 2, 1988

INVENTOR(S) : Broder, et al.

It is certified that error appears in the above-identified patent and that said Letters Patent is hereby corrected as shown below:

```
    Column 1, Line 45, change "HC 8755" to --HB 8755--.
    Column 2, Line 40, change "HC 8755" to --HB 8755--.
In the Claims:
    Claim 1, Line 2, change "HC 8755" to --HB 8755.
```

Signed and Sealed this

Twentieth Day of September, 1988

Attest:

DONALD J. QUIGG

Attesting Officer

Commissioner of Patents and Trademarks